(12) United States Patent
Sun et al.

(10) Patent No.: US 11,291,748 B2
(45) Date of Patent: Apr. 5, 2022

(54) EMBOLISM MATERIAL FOR BLOOD VESSEL, PREPARATION METHOD THEREFOR AND USE THEREOF IN PREPARATION OF DRUGS

(71) Applicant: ANEW-MED LIFE SCIENCE (WUHAN) CO., LTD, Hubei (CN)

(72) Inventors: Haixia Sun, Hubei (CN); Hong Liu, Hubei (CN); Han Li, Hubei (CN); Jian Zeng, Hubei (CN); Shuang Liu, Hubei (CN); Xin Lu, Hubei (CN); Juncheng Guo, Hubei (CN); Binghan Yuan, Hubei (CN); Ling Li, Hubei (CN)

(73) Assignee: ANEW-MED LIFE SCIENCE (WUHAN) CO., LTD, Wuhan (CN)

( * ) Notice: Subject to any disclaimer, the term of this patent is extended or adjusted under 35 U.S.C. 154(b) by 193 days.

(21) Appl. No.: 16/329,287

(22) PCT Filed: Dec. 23, 2016

(86) PCT No.: PCT/CN2016/111645
§ 371 (c)(1),
(2) Date: Feb. 28, 2019

(87) PCT Pub. No.: WO2018/040407
PCT Pub. Date: Mar. 8, 2018

(65) Prior Publication Data
US 2019/0247536 A1    Aug. 15, 2019

(30) Foreign Application Priority Data
Aug. 31, 2016 (CN) .......................... 201610781459.9

(51) Int. Cl.
*A61L 24/00* (2006.01)
*A61L 24/06* (2006.01)

(52) U.S. Cl.
CPC .............. *A61L 24/06* (2013.01); *A61L 24/00* (2013.01); *A61L 24/001* (2013.01); *A61L 2430/36* (2013.01)

(58) Field of Classification Search
CPC ........ A61L 24/06; A61L 24/00; A61L 24/001; A61L 2430/36
See application file for complete search history.

(56) References Cited

U.S. PATENT DOCUMENTS 6,486,213 B1 * 11/2002 Chen
2009/0053276 A1 * 2/2009 Richard
2013/0190788 A1 * 7/2013 Lowinger
2014/0363382 A1 * 12/2014 Campbell

FOREIGN PATENT DOCUMENTS

| CN | 1569909 | 1/2005 |
|---|---|---|
| CN | 1923303 | 3/2007 |
| CN | 101690831 | 4/2010 |
| CN | 102125516 | 7/2011 |
| CN | 104130348 | 11/2014 |
| CN | 104645356 | 5/2015 |
| CN | 105693920 | 6/2016 |
| JP | H05253283 | 10/1993 |

OTHER PUBLICATIONS

Liu et al. (Biomaterials, Published 2004, pp. 5659-5666) (Year: 2004).*
International Search Report (English) and Written Opinion dated May 31, 2017, from International Application No. PCT/CN2016/111645, 11 pages.
Liao, Y. "Preparation, Representation and Related Biological Assessment of Highly Concentrated Poly (N-isopropylamide-co-Butyl methacrylate) Nanogel Dispersions for Interventional Therapy for Liver Cancers", CMFD, Medicine and Public Health, No. 3, Mar. 15, 2017 [English abstract].
Donglai, L.,"The studies on the pilot tests and the quality standards of emperature-sensitive nanogels in the blood-vascular embolization therapy", Huazhong University of Science and Technology Master Degree Thesis, 59 pages [English abstract].
First Office Action and search report dated Nov. 1, 2018, for counterpart Chinese patent application No. 201610781459.9, 12 pages.
Second Office Action and search report dated Jan. 17, 2019, for counterpart Chinese patent application No. 201610781459.9, 7 pages.
Chinese search report dated Feb. 22, 2019, for counterpart Chinese patent application No. 201610781459.9, 3 pages.

* cited by examiner

*Primary Examiner* — Alma Pipic
(74) *Attorney, Agent, or Firm* — Meunier Carlin & Curfman LLC

(57) ABSTRACT

Provided are the use of poly(N-isopropylacrylamide-co-butyl methacrylate) in preparing an embolism material for blood vessels, an embolism material for blood vessels and the use thereof in preparation of drugs. The embolism material for blood vessels comprises poly(N-isopropylacrylamide-co-butyl methacrylate) and a dispersion medium consisting of an electrolyte, a contrast agent, a pH regulator and water. The concentrations of the polymer, electrolyte and contrast agent are respectively 5-30 mg/ml, 0.1-30 mg/ml and 100-350 mg/ml based on iodine. The embolism material for blood vessels is suitable for embolization therapy of tumors in hypervascular and parenchymal visceral organs.

13 Claims, 4 Drawing Sheets

EMBOLISM MATERIAL FOR BLOOD VESSEL, PREPARATION METHOD THEREFOR AND USE THEREOF IN PREPARATION OF DRUGS

FIELD OF INVENTION

The invention belongs to the technical field of blood vessel embolic materials for medical device interventions, specifically, to use of poly(N-isopropylacrylamide-co-butyl methacrylate) in the preparation of a blood vessel embolic material, a blood vessel embolic material comprising poly (N-isopropylacrylamide-co-butyl methacrylate) and a dispersion medium, a method for preparation thereof, and use thereof in the manufacture of a medicament.

BACKGROUND ART

Interventional therapy comes from the creative idea and practice of angiographic diagnosis and angiography. It is a technique based on imaging diagnosis and using medical imaging diagnostic equipment such as DSA, CT and MRI as a guide to diagnose and treat diseases. It has the characteristics of small trauma, accurate positioning, high efficacy, less complications, a quick effect, and high reproducibility. In addition to internal medicine treatment and surgical treatment, interventional therapy has become the third most common clinical treatment means.

The most widely used interventional therapy in clinical settings is transcatheter arterial embolization (TCE) and transcatheter arterial chemoembolization (TACE), mainly used for treatment of advanced tumors. Such methods enable accurate injection of drugs into the pathological site, and at the same time embolization of the arteries supplying blood for the tumor, thereby effectively blocking the blood supply, and leading to ischemia and necrosis of the tumor, while causing few toxic side effects to tissue cells in other parts of the body, and exhibiting a distinctive therapeutic effect.

An important factor in interventional embolization is the choice of vascular embolic agent, which directly determines the therapeutic effect. Blood vessel embolic materials used for tumor treatment are required to have the following characteristics: 1) good fluidity, which allows easy injection through a catheter without sticking to or clogging the catheter; 2) reasonable gelation time, which allows easy diffusion and filling into the peripheral blood vessels of a tumor, to cast the tumor peripheral blood vessels; 3) reasonable embolism strength, which allows resistance to blood flow scouring and long-term maintenance of blood vessel embolization; 4) good visibility, i.e., X-ray shielding ability, which allows the embolic agent to be guided and delivered to the correct target site; and 5) long-lasting controlled release of anti-tumor drugs. However, as far as the above criteria are concerned, there is currently no embolic agent available on the market that can be a "panacea", and development of various embolic agents has been necessary to meet the clinical demands.

The poly(N-isopropylacrylamide) type temperature-sensitive polymer, as a liquid embolic material, has a lower viscosity in the sol state, as well as good thixotropy, a fast gelation speed, and good biocompatibility, which make it a research hotspot for blood vessel embolic materials for interventional medical devices.

Chinese patent application CN1923303A discloses a temperature-sensitive nanogel system for blood vessel embolic materials, comprising a poly(N-isopropylamide)-based polymer nanogel and a dispersion medium. This blood vessel embolization system is characterized by good in vitro fluidity and fast sol-gel phase transition speed, and is suitable for blood vessel embolism in tumors and treatment of diseases such as arteriovenous malformation. However, this blood vessel embolization system is disadvantageous in that 1) although its fluidity is superior to solid embolic materials, its viscosity is high, and its fluidity is still lower than that of the currently clinically used super-liquefied lipiodol, causing certain difficulty in injection when used clinically; and 2) the sol-gel phase transition rate is too fast such that when used clinically the operation time is short, which increases the difficulty in operation by clinicians.

Chinese patent application CN1569909A discloses a temperature-sensitive polymer and a method for preparation thereof, wherein the temperature-sensitive polymer is obtained by forming a copolymer of N-isopropylacrylamide and N-n-propylacrylamide as monomers; the polymer is formulated into an aqueous solution, and a suitable conrast agent is added, to obtain a blood vessel embolic material, which rapidly precipitates at the body temperature and embolizes the diseased blood vessel, thereby achieving therapeutic purposes. It is mainly applied to cerebral arteriovenous malformation (AVM), but tumor embolism for liver cancer, renal cancer, or the like is not mentioned.

Chinese patent application CN101690831A discloses a temperature-sensitive gel-based blood vessel embolic material, including a poly(N-isopropylacrylamide)-based polymer nanogel and a dispersion medium, wherein the dispersion medium is a water-soluble iodine-containing contrast agent injection or a diluent thereof. As for the temperature-sensitive gel blood vessel embolic material, the phase transition temperature of the blood vessel embolic material and the minimum nanogel content required for embolization can be adjusted according to factors such as the type and amount of the copolymer in the nanogel and the amount of the crosslinking agent, and also the type and content of the contrast agent, so as to obtain the visualizable temperature-sensitive gel blood vessel embolic material displaying a low viscosity and a good embolization performance. However, the temperature-sensitive gel blood vessel embolic material provided in this invention still has the following disadvantages: 1) although the viscosity of the blood vessel embolic material is lowered by adjustment of the type and content of the contrast agent, its fluidity is still not comparable to that of the super-liquefied lipiodol, and still causes the problem of difficult injection in clinical operations; and 2) the problem of dissolution during use of the blood vessel embolic material remains unsolved, and poses a risk of disintegration by the flushing of blood flow during clinical use.

Chinese patent application CN104130348A discloses a temperature-sensitive liquid embolic material, consisting of a polymer of poly(N-isopropylacrylamide-co-butyl methacrylate), a conrast agent and a solvent. The liquid embolic material with a polymer concentration of 5% was selected to perform a renal arterial embolization experiment on domestic pigs, in which the renal artery on one side of the pigs was successfully embolized, no catheter clogging occurred during embolization, and the catheter was smoothly removed, indicating that it is easy to judge the starting and end points of the embolic material and to introduce the microcatheter, and the biocompatibility is good. However, the liquid embolic material provided in this invention still has the following defects. Since the poly(N-isopropylacrylamide-co-butyl methacrylate) in the blood vessel embolic material provided in this invention is a linear polymer, the embolization strength is insufficient at a low concentration. This is specifically manifested in that in the in vitro simulation experiment, the glass beads are difficult to embolize and are easily flushed away. When the concentration is high, the diffusivity is poor, such that it only embolizes the upper end of the glass beads. Therefore, the blood vessel embolic material of this invention has poor diffusivity and a risk of being easily disintegrated by the flushing of blood flow during clinical use, and thus does not essentially solve the safety issue in interventional embolization caused by disintegration of an embolic material after leaving a microcatheter.

SUMMARY OF THE INVENTION

In order to solve the problems in the prior art, the present invention provides a blood vessel embolic material, of which the composition has a very low viscosity at room temperature and is in a sol state with good fluidity comparable to that of super-liquefied lipiodol. It turns into a solid gel state at body temperature, and its gelation kinetics can be regulated. It is mainly used for blood vessel embolization treatment of blood-rich tumors (such as liver cancer, kidney cancer, etc.). It is highly controllable in clinical operations, does not stick to or clog microcatheters, and is easy to inject. After entering blood vessels, it results in in situ "casting" embolization of the blood vessels from the peripheral blood vessel to the aorta in a diffusive filling manner, which effectively suppresses establishment of collateral circulation of tumor blood vessels and improves the therapeutic effect on the tumor. It has suitable gel strength, resistance to blood flow scouring, and a performance superior to lipiodol, and can permanently embolize target vessels. It has an ideal visualization performance, and avoids problems such as safety risks caused by operations such as blending with the contrast agent right before clinical use and insufficient clarity after visualization. The blood vessel embolic material comprising a chemotherapeutic agent allows controlled release of the chemotherapeutic agent, achieves a combinational therapy of chemotherapy and embolization, and effectively inhibits tumor growth.

In order to achieve the above technical purposes, the present invention provides the following technical solutions.

Provided is use of poly(N-isopropylacrylamide-co-butyl methacrylate) in the preparation of a blood vessel embolic material, wherein the poly(N-isopropylacrylamide-co-butyl methacrylate) is a crosslinked polymer produced by thermally initiated radical polymerization of N-isopropylacrylamide as a monomer, N,N'-dimethylenebisacrylamide as a crosslinking agent, and butyl methacrylate as a comonomer by a soap-free emulsion polymerization method.

Further provided is the use of poly(N-isopropylacrylamide-co-butyl methacrylate) in the preparation of a blood vessel embolic material, wherein the poly(N-isopropylacrylamide-co-butyl methacrylate) has the following structural formula:

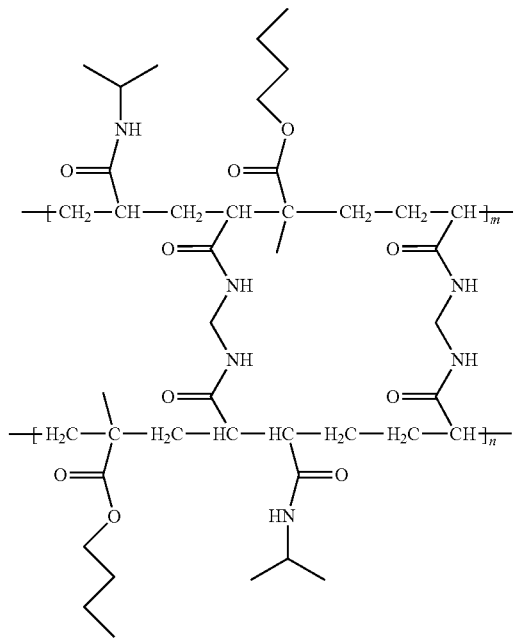

wherein, m and n indicate a certain number of repeating units, and has no specific numerical range; the poly(N-isopropylacrylamide-co-butyl methacrylate) is spherical, and optionally, the poly(N-isopropylacrylamide-co-butyl methacrylate) has an intrinsic viscosity of 40 to 100 ml/g.

Provided is a blood vessel embolic material, comprising a dispersion medium and poly(N-isopropylacrylamide-co-butyl methacrylate), wherein the poly(N-isopropylacrylamide-co-butyl methacrylate) is a crosslinked polymer.

Further provided is the blood vessel embolic material, wherein the poly(N-isopropylacrylamide-co-butyl methacrylate) has the following structural formula:

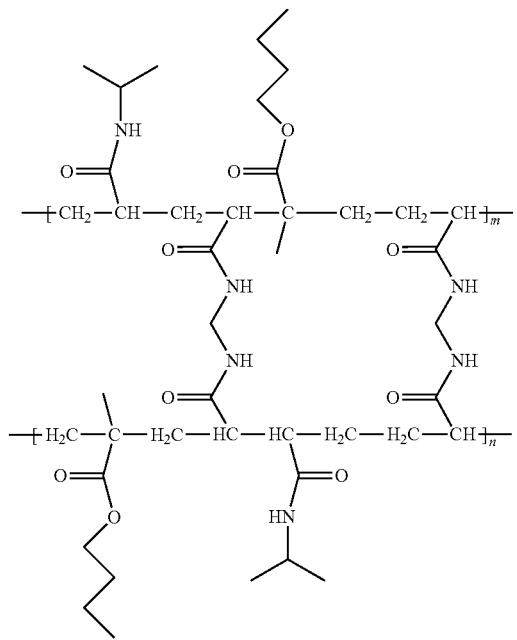

wherein, m and n indicate a certain number of repeating units, and has no specific numerical range; the poly(N- isopropylacrylamide-co-butyl methacrylate) is spherical, and optionally, the poly(N-isopropylacrylamide-co-butyl methacrylate) has an intrinsic viscosity of 40 to 100 m/g.

Further provided is the blood vessel embolic material, wherein the dispersion medium comprises an electrolyte, a conrast agent, a pH regulator, and water; wherein the electrolyte is at least one selected from the group consisting of sodium chloride, sodium hydroxide, calcium chloride, disodium hydrogen phosphate, sodium dihydrogen phosphate, and calcium disodium edetate; the conrast agent includes an iodine-containing polyol, where the iodine-containing polyol is at least one of iohexol, ioversol, iopamidol or iobitridol; the pH regulator includes hydrochloric acid. Preferably, the blood vessel embolic material has a pH of 6.5 to 8.0.

Further provided is the blood vessel embolic material, wherein the dispersion medium further comprises an iodine-free polyol, and the iodine-free polyol includes at least one selected from the group consisting of calcium disodium edetate, mannitol, Tween-80, poly(ethylene glycol) 200, poly(ethylene glycol) 400, and (polyethylene glycol) 600.

Further provided is the blood vessel embolic material, comprising 5 to 30 mg of the poly(N-isopropylacrylamide-co-butyl methacrylate), 0.1 to 30 mg of the electrolyte, and 100 to 350 mg of the iodine-containing polyol in terms of iodine, per milliliter of the blood vessel embolic material. Further preferably, one milliliter of the blood vessel embolic material comprises 10 to 20 mg of the poly(N-isopropylacrylamide-co-butyl methacrylate), 0.1 to 30 mg of the electrolyte, and 150 to 240 mg of the iodine-containing polyol in terms of iodine.

The iodine-containing polyol is measured in terms of iodine, and is calculated as follows. Iohexol, taken as an example, has a formula of $C_{19}H_{26}I_3N_3O_9$ and a molecular weight of 821.1. The amount in terms of iodine is calculated by the equation $$I = \frac{3M_I}{M_0 V_0} \times m_0$$

(wherein $M_I$ is the molecular weight of iodine, 126.9; $M_0$ is the molecular weight of iohexol, 821.1; $m_0$ is the mass of iohexol in mg; and $V_0$ is the volume of the solution in ml).

Further provided is the blood vessel embolic material, comprising 5 to 30 mg of the poly(N-isopropylacrylamide-co-butyl methacrylate), 0.1 to 30 mg of the electrolyte, 100 to 350 mg of the iodine-containing polyol in terms of iodine, and 0.1 to 10 mg of the iodine-free polyol, per milliliter of the blood vessel embolic material; and further preferably, comprising 10 to 20 mg of the poly(N-isopropylacrylamide-co-butyl methacrylate), 0.1 to 30 mg of the electrolyte, 150 to 240 mg of the iodine-containing polyol in terms of iodine, and 0.1 to 10 mg of the iodine-free polyol, per milliliter of the blood vessel embolic material.

Further provided is the blood vessel embolic material, further comprising a chemotherapeutic agent, which is at least one selected from the group consisting of doxorubicin hydrochloride, epirubicin hydrochloride, mitomycin C or fluorouracil.

Provided is a method for preparing a blood vessel embolic material, specifically, comprising steps of:

(1) adding an electrolyte and an iodine-free polyol to a solution containing poly(N-isopropylacrylamide-co-butyl methacrylate) and a conrast agent and mixing them at 0 to 30° C.;

(2) adjusting the pH of the solution obtained in step (1) to 6.5 to 8.0 with a pH regulator, to obtain the blood vessel embolic material.

Provided is use of the blood vessel embolic material in the manufacture of a medicament, wherein the medicament is for treatment of cancer, and furthermore, the medicament is for treatment of cancer by chemoembolization.

Through the above technical solutions, the present invention produces the following beneficial effects:

1. The blood vessel embolic material according to the present invention comprises the poly(N-isopropylacrylamide-co-butyl methacrylate) crosslinked polymer with a suitable intrinsic viscosity. The presence of the iodine-free polyol, the iodine-containing polyol contrast agent and the electrolyte in the dispersion medium further decreases the viscosity of the composition. Therefore, the blood vessel embolic material has a very low viscosity at room temperature and good fluidity comparable to that of ultra-liquefied lipiodol. When in use, it does not stick to or clog catheters, is easy to inject, and has good operability.

2. In the blood vessel embolic material according to the present invention, the electrolyte in the dispersion medium can promote gelation and cooperate with the polyol in the dispersion medium to render the blood vessel embolic material according to the present invention a reasonable gelation time, i.e. 40 to 80 s, which enhances operational controllability in clinical practice. At the same time, the presence of the dispersion medium provides a good phase-transition environment for the polymer, such that the blood vessel embolic material is not dissolved during its passage from the microcatheter to the targeted ends of blood vessels and can sufficiently fill the ends of the blood vessels to perform casting, thereby being suitable for embolization of various foci.

3. In the blood vessel embolic material according to the present invention, the electrolyte in the dispersion medium can promote gelation such that the blood vessel embolic material has suitable gel strength to resist blood flow scouring and has a low escaping ratio, and can effectively prevent mis-occlusion and de-occlusion of blood vessels due to incomplete embolization. At the same time, it also reduces the probability of establishment of tumor collateral circulation, fulfills the purpose of permanent embolization of tumor peripheral blood vessels, and effectively inhibits tumor growth.

4. The blood vessel embolic material according to the present invention can be visualized under fluoroscopy with a suitable choice of conrast agent, and enter the peripheral blood vessels at high density. This avoids the safety risk caused by the shortcomings of large operational errors, nonuniform sample mixing, and a long preparation time required by the premixing of conventional embolic agents with a contrast agent before surgery. At the same time, it can effectively monitor the phase transition behavior of the blood vessel embolic material, and effectively prevents mis-occlusion and reflow.

5. The blood vessel embolic material according to the present invention comprises a water-soluble chemotherapeutic agent such as doxorubicin hydrochloride, epirubicin hydrochloride, mitomycin C or fluorouracil. Through interventional chemoembolization, it achieves the purposes of controlled release of the chemotherapeutic agent, and combinational treatment with chemotherapy and vascular embolization, which effectively inhibit tumor growth.

DETAILED DESCRIPTION OF PREFERRED EMBODIMENTS

Figure 1:
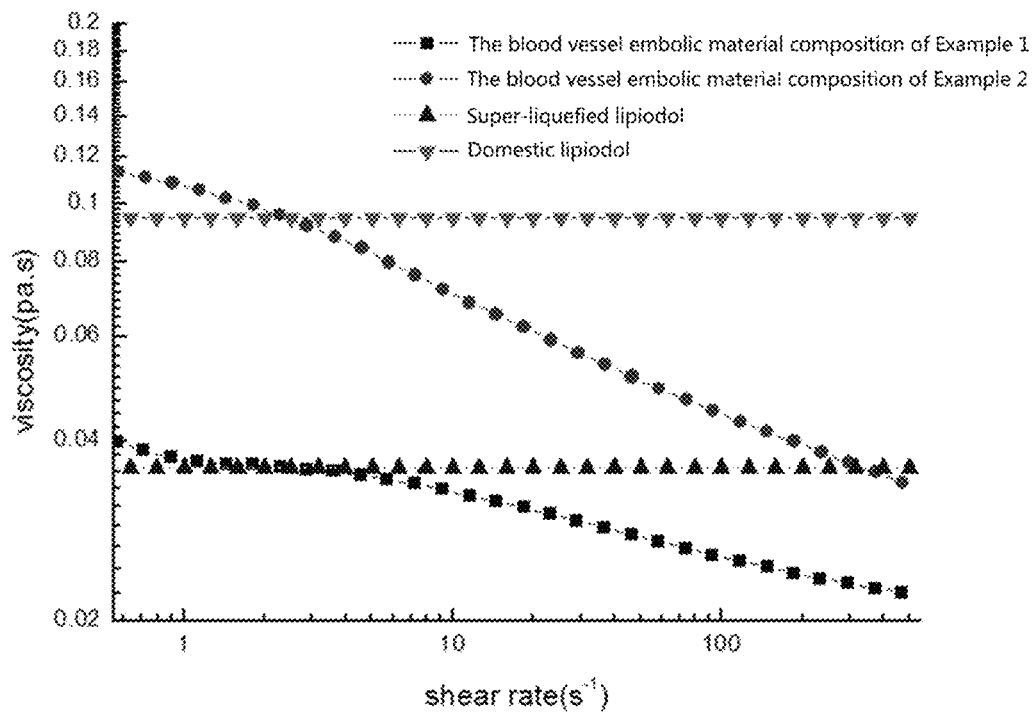
FIG. 1 shows a graph comparing the viscosity of the blood vessel embolic material of Example 1, the blood vessel embolic material of Example 2, a domestic lipiodol and a super-liquefied lipiodol.

The poly(N-isopropylacrylamide-co-butyl methacrylate) was prepared by thermally initiated radical polymerization of N-isopropylacrylamide as a monomer, N,N'-dimethylenebisacrylamide as a crosslinking agent, and butyl methacrylate as a comonomer by a soap-free emulsion polymerization method (see the Master's thesis of Huazhong University of Science and Technology, "Preparation, Characterization and Related Biological Evaluation of High Concentration Poly (N-isopropylacrylamide-co-butyl methacrylate) Nanogel Dispersion for Interventional Therapy for Liver Cancer", LIAO Yuanxia, page 12).

Example 1

Step 1: At 0 to 30° C., 10.0 g of poly(N-isopropylacrylamide-co-butyl methacrylate) having an intrinsic viscosity of 68 ml/g and 259 g of iohexol powder as a contrast agent were added to 400 ml water and stirred well, to obtain a solution containing poly(N-isopropylacrylamide-co-butyl methacrylate) and the contrast agent. To this solution, 1.25 g of calcium chloride as an electrolyte and 0.3 g of mannitol as an iodine-free polyol were added, made up to 500 ml, and mixed well.

Step 2: the pH of the solution obtained in Step 1 was adjusted to 6.5 to 8.0 with hydrochloric acid as a pH regulator, so as to obtain a blood vessel embolic material containing poly(N-isopropylacrylamide-co-butyl methacrylate) at a mass/volume concentration of 20 mg/ml, calcium chloride at a mass/volume concentration of 2.5 mg/ml, mannitol at a mass/volume concentration of 0.6 mg/ml, and iohexol at a mass/volume concentration of 240 mg/ml in terms of iodine.

The amount by mass and intrinsic viscosity of poly(N-isopropylacrylamide-co-butyl methacrylate), the amount by mass of the contrast agent, the amount by mass of the electrolyte, and the amount by mass of the iodine-free polyol of Examples 2 to 10 are shown in Table 1, and the rest of the preparation process was the same as that of Example 1.

Examples 2 to 10

TABLE 1

List of mass and intrinsic viscosity of poly(N-isopropylacrylamide-co-butyl methacrylate)(abbreviated as Polymer), contrast agent mass, electrolyte mass and iodine-free polyol mass of Examples 2 to 10.

| Example | Polymer mass | Polymer intrinsic viscosity | Contrast agent mass | Electrolyte mass | Iodine-free polyol mass |
|---|---|---|---|---|---|
| 2 | 2.5 g | 40 ml/g | 102 g of iopamidol | 1.25 g of calcium disodium edetate | 0.35 g of mannitol, 0.30 g of tromethamine |
| 3 | 7.5 g | 60 ml/g | 159 g of ioversol | 1.25 g of calcium hydroxide | 0.35 g of mannitol, 0.30 g of tromethamine |
| 4 | 12.5 g | 80 ml/g | 259 g of iohexol | 0.75 g of disodium hydrogen phosphate, 0.50 g of calcium disodium edetate | 0 g |
| 5 | 15.0 g | 100 ml/g | 357 g of iopamidol | 0.75 g of sodium hydroxide, 0.50 g of sodium dihydrogen phosphate | 0 g |
| 6 | 5.0 g | 68 ml/g | 259 g of iohexol | 0.50 g of sodium chloride | 1.00 g of Tween-80 |
| 7 | 10.0 g | 68 ml/g | 259 g of iohexol | 0.05 g of disodium hydrogen phosphate | 2.50 g of mannitol |
| 8 | 10.0 g | 68 ml/g | 259 g of iohexol | 1.00 g of sodium chloride, 1.00 g of calcium chloride, 0.5 g of sodium dihydrogen phosphate | 0.05 g of polyethylene glycol 600 |
| 9 | 5.0 g | 68 ml/g | 259 g of iohexol | 3.00 g of sodium chloride, 1.00 g of calcium chloride, 1.00 g of calcium disodium edetate | 0.05 g of polyethylene glycol 200 |
| 10 | 7.5 g | 68 ml/g | 259 g of iohexol | 8.00 g of sodium chloride 7.00 g of calcium disodium edetate | 5.00 g of tromethamine |

Example 11

In this example, doxorubicin hydrochloride was added to the blood vessel embolic material of Example 1. Specifically, 2 ml to ml was taken from 5 ml of the blood vessel embolic material of Example 1 with a 10 ml syringe, and injected into 50 mg of doxorubicin hydrochloride for injection (Haizheng Pfizer Pharmaceutical Co., Ltd.). The mixture was shaken for 5 minutes at room temperature on a vortexer, and then allowed to stand for half an hour. The subnatant was taken to obtain the blood vessel embolic material of Example 11.

Comparative Example 1

A blood vessel embolic material containing no electrolyte or iodine-free polyol was prepared as follows.

Step 1: At 0 to 30° C., 10.0 g of poly(N-isopropylacrylamide-co-butyl methacrylate) having an intrinsic viscosity of 68 ml/g and 259 g of iohexol powder as a contrast agent were added to 500 ml water and stirred well.

Step 2: the pH of the solution obtained in Step 1 was adjusted to 6.5 to 8.0 with hydrochloric acid as a pH regulator, so as to obtain a blood vessel embolic material containing poly(N-isopropylacrylamide-co-butyl methacrylate) at a mass/volume concentration of 20 mg/ml and the contrast agent iohexol at a mass/volume concentration of 240 mg/ml in terms of iodine.

Comparative Example 2

A blood vessel embolic material containing linear poly(N-isopropylacrylamide-co-butyl methacrylate) was prepared as follows.

Step 1: 2.263 g of N-isopropylacrylamide, 0.032 g of sodium dodecyl sulfate and 0.168 ml of butyl methacrylate were dissolved in 160 ml of purified water under stirring. Under $N_2$ protection, the temperature was raised to 70° C., and a 10 ml aqueous solution of a 9.5 mg/ml potassium persulfate was added and allowed to react for 4.5 hours. The reaction solution was purified by dialysis and lyophilized to obtain the linear polymer of poly(N-isopropylacrylamide-co-butyl methacrylate) as a solid for use.

Step 2: 10.0 g of the solid for use in Step 1 and 259 g of iohexol powder as a contrast agent were weighed and added to 400 ml water and mixed well, so as to obtain a solution containing the linear poly(N-isopropylacrylamide-co-butyl methacrylate) and the contrast agent. Subsequently, to this solution, 1.25 g of calcium chloride as an electrolyte and 0.3 g of mannitol as an iodine-free polyol were added, made up to 500 ml, and mixed well.

Step 3: the pH of the solution obtained in Step 2 was adjusted to 6.5 to 8.0 with hydrochloric acid as a pH regulator, so as to obtain a blood vessel embolic material containing the poly(N-isopropylacrylamide-co-butyl methacrylate) linear polymer at a mass/volume concentration of 20 mg/ml, calcium chloride at a mass/volume concentration of 2.5 mg/ml, mannitol at a mass/volume concentration of 0.6 mg/ml, and iohexol at a mass/volume concentration of 240 mg/ml in terms of iodine.

Table 2 shows the test results of the performance of the blood vessel embolic materials of Examples 1 to 10 and Comparative Examples 1 and 2.

TABLE 2

Performance indices of the blood vessel embolic materials of Examples 1 to 10 and Comparative Examples 1 and 2.

| No. | Viscosity (mPa · s) | In vitro gelation time (S) | Modulus (gel/sol) | Gelation temperature (° C.) | Escaping ratio | Dissolution or not | Free iodine concentration (μg/g) |
|---|---|---|---|---|---|---|---|
| Example 1 | <35 | 50~60 | >100 | 31.5~35.5 | <10% | No | ≤60 |
| Example 2 | <35 | 70~80 | >100 | 31.5~35.5 | <10% | No | ≤60 |
| Example 3 | <35 | 50~60 | >100 | 31.5~35.5 | <10% | No | ≤60 |
| Example 4 | <35 | 50~60 | >100 | 31.5~35.5 | <10% | No | ≤60 |
| Example 5 | <35 | 40~50 | >100 | 31.5~35.5 | <10% | No | ≤60 |
| Example 6 | <35 | 50~65 | >100 | 31.5~35.5 | <10% | No | ≤60 |
| Example 7 | <35 | 50~65 | >100 | 31.5~35.5 | <10% | No | ≤60 |
| Example 8 | <35 | 50~65 | >100 | 31.5~35.5 | <10% | No | ≤60 |
| Example 9 | <35 | 50~65 | >100 | 31.5~35.5 | <10% | No | ≤60 |
| Example 10 | <35 | 50~65 | >100 | 31.5~35.5 | <10% | No | ≤60 |
| Comparative example 1 | 16.8 | >180 | >100 | — | >80% | Yes | ≤60 |
| Comparative example 2 | 56.7 | 15~20 | >100 | 34.1 | <10% | No | ≤60 |

The test results shown in Table 2 demonstrate that the blood vessel embolic material according to the present invention has a reasonable gelation time, regulatable gelation kinetics, suitable gel strength, resistance to blood flow scouring, and a performance superior to lipiodol. It can permanently embolize target vessels, has an ideal visualization performance, and avoids problems such as safety risks caused by operations such as blending with the contrast agent right before clinical use and insufficient clarity after visualization.

At the same time, it can be seen from the test result of Comparative example 1 that when the blood vessel embolic material does not contain an electrolyte, its in vitro gelation time is too long, so that it is easy to dissolve, cannot well cast the ends of blood vessels, and the escaping ratio is high, allowing easy mis-occlusion.

At the same time, it can be seen from the test result of Comparative example 2 that when the poly(N-isopropylacrylamide-co-butyl methacrylate) of the blood vessel embolic material is a linear polymer, it has a viscosity significantly higher than that of Example 1 and relatively poor fluidity under the same conditions. Moreover, its in vitro gelation time is too short, which means a short operation time in clinical use, which increases the difficulty in operation by clinicians. During the interventional therapy, there is not enough time for it to enter and cast the ends of blood vessels.

FIG. 1 shows a comparison of shear thinning and viscosity of the blood vessel embolic material of Example 1, the blood vessel embolic material of Comparative example 2, a domestic lipiodol, and a super-liquefied lipiodol.

It can be seen from the results of the viscosity test in Table 2 and the viscosity curve in FIG. 1 that both the blood vessel embolic material composition of Example 1 and the blood vessel embolic material composition formulated with a linear polymer in Comparative example 2 have a shear thinning property. However, under the same conditions, the viscosity of the blood vessel embolic material according to the present invention is significantly lower than that of the blood vessel embolic material composition formulated with the linear polymer, and is also significantly lower than that of the domestic lipiodol and is comparable to that of the super-liquefied lipiodol.

Experimental Example 1

A simulation experiment for the in vitro release of the blood vessel embolic material according to Example 11 was performed using a drug eluting device which can well simulate the distribution and release of the drug released in vivo from transcatheter arterial chemoembolization (TACE).

The drug eluting device includes a glass release cell, a peristaltic pump, an oil bath, a thermometer, a conical flask, a beaker, and connecting pipes. The glass release cell is a customized glass cell which is 2 cm in diameter and 2 cm in height and has its top closed with a glass stopper. Both ends of the glass release cell can each be connected with a connecting pipe. The conical flask was placed in the oil bath, and then the conical flask, the peristaltic pump, the glass release cell, and the beaker were sequentially connected through connecting pipes.

The entire device was placed in a dark environment. In the experiment, the temperature of the oil bath was adjusted to 37° C., the flow rate of the peristaltic pump was adjusted to 10 rpm, then the oil bath was opened, 0.01 M PBS as a release liquid was injected into the conical flask which was then placed in the oil bath, and the temperature was monitored with the thermometer to ensure that the temperature of release liquid was 37° C. Thereafter, the glass stopper was removed from the glass release cell. 50 μL of the blood vessel embolic material loaded with doxorubicin according to Example 11 was pipetted and injected into the glass release cell, and spread over the bottom of the release cell. The glass release cell was then covered with the glass stopper. Subsequently, the peristaltic pump was started to provide power. When the liquid flowed into the release cell, timing was started. Samples were taken from the beaker at regular intervals to determine the fluorescence intensity of the samples. The cumulative release rate of doxorubicin hydrochloride was calculated according to the following formulae.

Cumulative release $S_n = C_1 \times V_1 + C_2 \times V_2 + \ldots + C_n \times V_n$ $M_{Dox} = V_{gel} \times \rho_{Dox}$ Cumulative release rate (%) = $S_n / M_{Dox} \times 100$ wherein, n means the $n^{th}$ hour, $V_n$ is the volume released in the $n^{th}$ hour, and $C_n$ is the concentration of doxorubicin hydrochloride in the release liquid in the $n^{th}$ hour. $M_{Dox}$ is the content of doxorubicin hydrochloride in the doxorubicin hydrochloride-loaded gel. $V_{gel}$ is the volume of the doxorubicin hydrochloride-loaded gel added in the release cell. $\rho_{Dox}$ is the concentration of doxorubicin hydrochloride in the doxorubicin hydrochloride-loaded gel.

Figure 2:
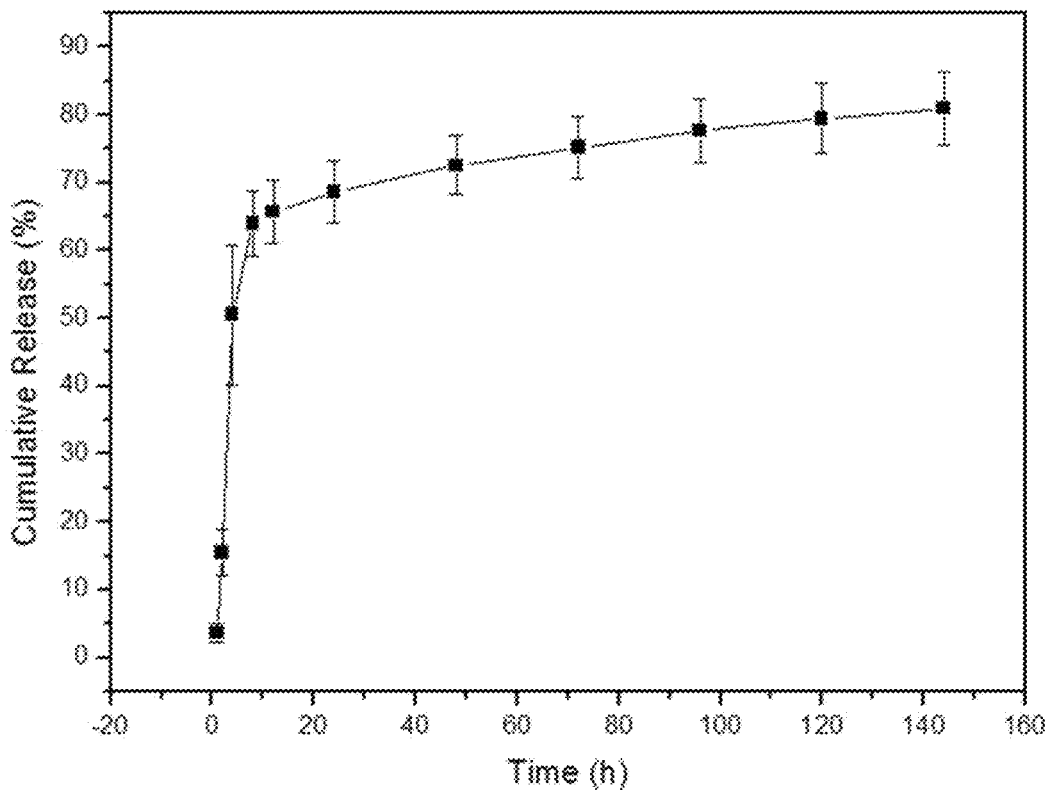
FIG. 2 shows the in vitro release profile of Experimental example 1.

FIG. 2 shows the 7-day in vitro release profile of Experimental example 1. The results show that the blood vessel embolic material according to the present invention can be used in combination with a chemotherapeutic agent and has the ability to slowly release the medicament in a controlled manner.

Experimental Example 2

The blood vessel embolic material of Example 1 was used for interventional embolization of the renal artery of normal rabbits.

Figure 3:
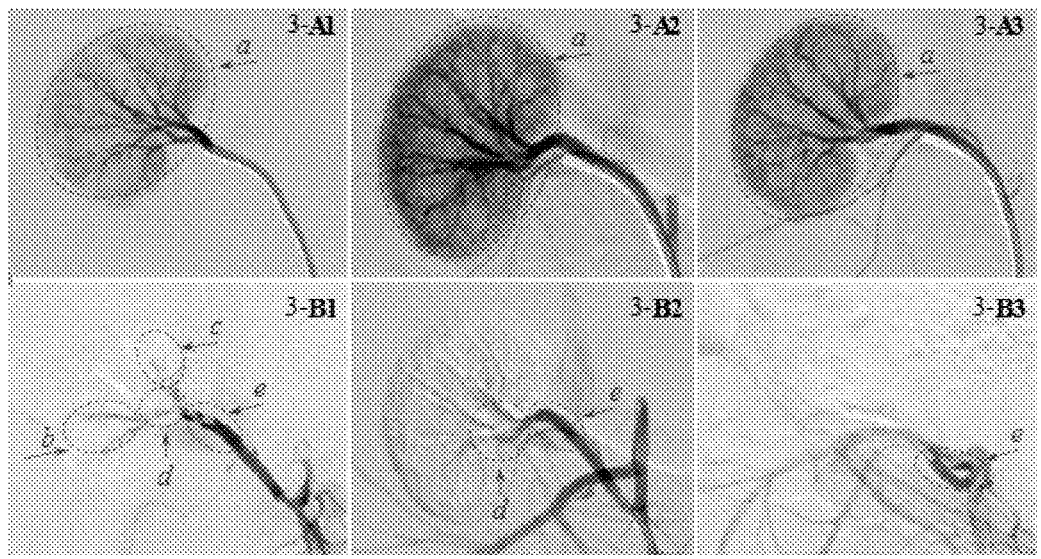
FIG. 3 shows Digital Subtraction Angiography (DSA) effect images of Experimental example 2.

FIG. 3 shows the Digital Subtraction Angiography (DSA) effect images of the interventional embolization of the renal artery of normal rabbits using the blood vessel embolic material according to Experimental example 2.

FIGS. 3-A1 to 3-A3 are angiographic DSA images before the interventional embolization of rabbit renal artery. FIGS. 3-B1 to 3-B3 are the respective contrast examination images after the interventional embolization, wherein the amount of blood vessel embolic material used in 3-B1 was 0.5 ml, the amount of blood vessel embolic material used in 3-B2 was 1.0 ml, and the amount of blood vessel embolic material used in 3-B3 was 2.0 ml. In the figures, a indicates renal peripheral blood vessels, b and c indicate small arterial blood vessels, and d and e indicate large arterial blood vessels.

The results shown in FIG. 3 indicate that different levels of renal artery embolization can be achieved by controlling the amount of blood vessel embolic material. In clinical practice, doctors can choose the amount of blood vessel embolic material to be used according to the tumor site. The operability of blood vessel embolic material in clinical practice is further improved.

Experimental Example 3

The blood vessel embolic material of Example 1 was used for interventional embolization of the right posterior renal artery of normal rabbits.

30 healthy Japanese White Rabbits which had been dry-fasted for 12 hours before the experiment were subjected to femoral artery intubation. After successful intubation, renal artery intubation was performed. Thereafter, renal artery embolization (RAE) was performed, followed by renal artery extubation, femoral artery extubation, and postoperative management. At each of four time points, i.e., one week, one month, two months, and three months after RAE, five post-embolization rabbits were randomly selected for contrast examination. Pathological observations were performed after four contrast examinations.

Figure 4:
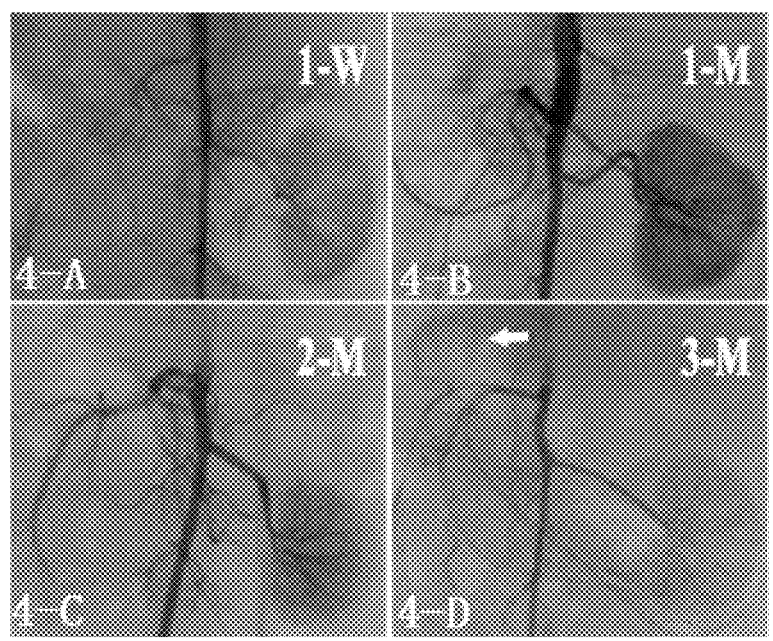
FIG. 4 shows the DSA contrast images at four examination time points of Experimental example 3.

FIG. 4 shows DSA contrast examination images at the four examination time points of Experimental example 3. FIGS. 4-A to 4-D are the DSA contrast examination images at 1 week, 1 month, 2 months, and 3 months, respectively.

The results show that no recanalization of the right renal artery or formation of collateral circulation was observed at the four preset examination time points, i.e. 1 week, 1 month, 2 months, and 3 months. This indicates that the blood vessel embolic material according to the present invention enables effective and long-term embolization of the targeted blood vessels.

Figure 5:
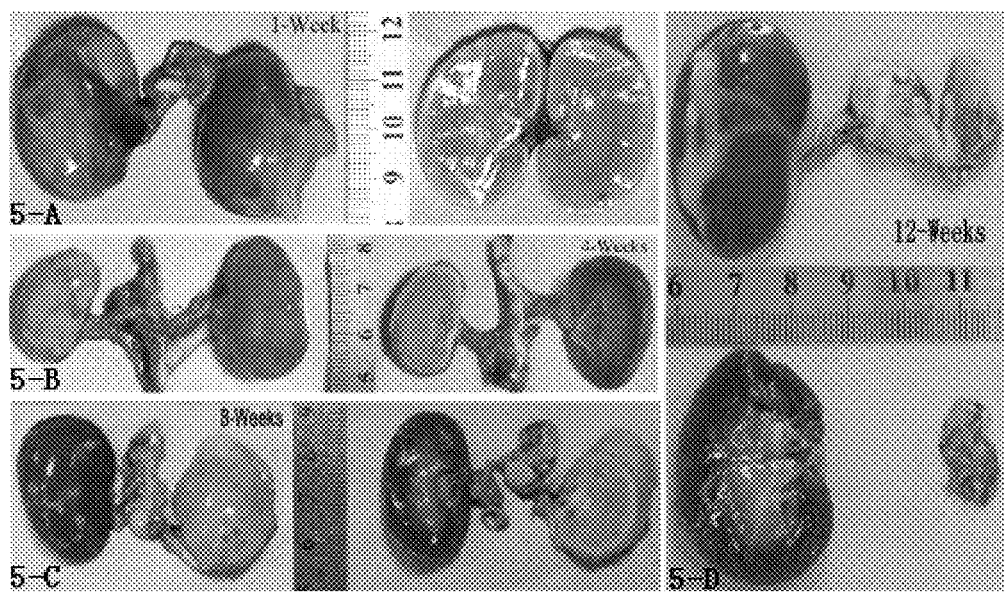
FIG. 5 shows the gross histopathological photographs at the four examination time points of Experimental example 3.

FIG. 5 shows the gross histopathological photographs at the four examination time points of Experimental example 3. FIGS. 5-A to 5-D are gross histopathological photographs corresponding to the examinations at 1 week, 1 month, 2 months, and 3 months, respectively.

The results show that, at later examination time points, the embolized kidney gradually shrank, while the contralateral kidney enlarged in compensation to different extents. This indicates that the blood vessel embolic material according to the present invention enables effective embolization of the targeted blood vessels.

Experimental Example 4

The blood vessel embolic material of Example 1, an equal amount of lipiodol+gelatin sponge, and an equal amount of saline were each used for interventional treatment of VX2 tumor-bearing rabbits. Specifically, after successful femoral artery intubation, renal artery intubation was performed, followed by extubation and postoperative management. MRI examination was performed one week after the operation.

Figure 6:
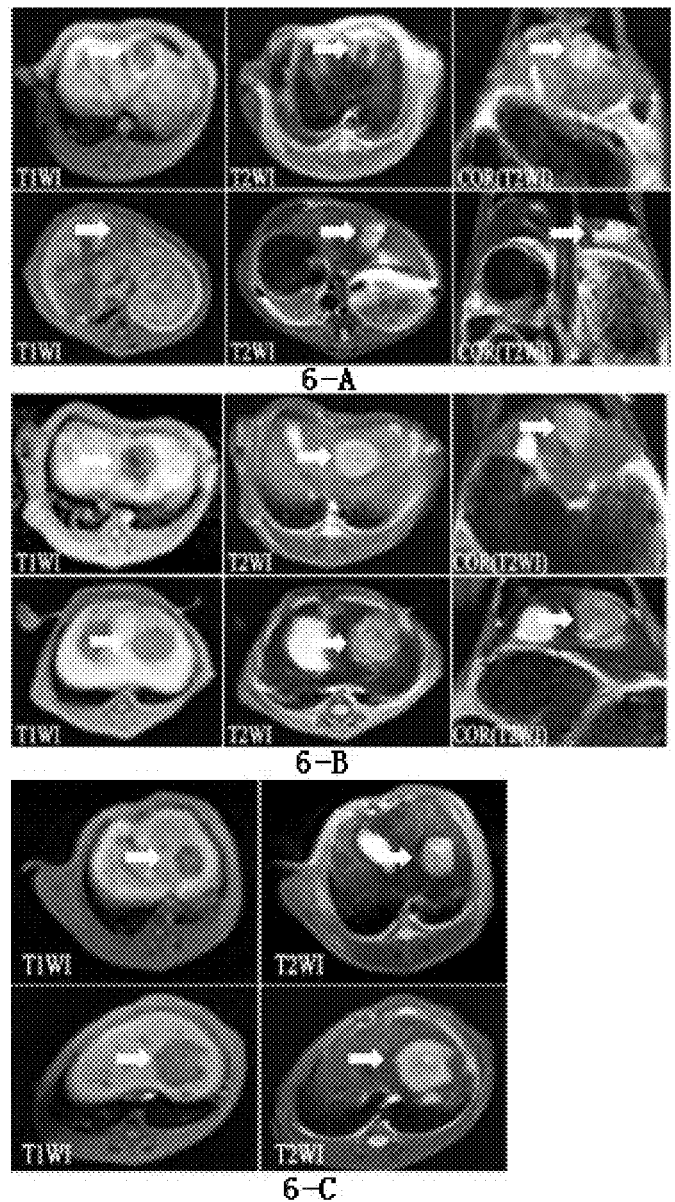
FIG. 6 shows MR effect images before and after interventional treatment of Experimental example 4.

FIG. 6 shows the MR images before and after the interventional treatment. FIGS. 6-A to 6-C correspond to the MR images with the blood vessel embolic material of Example 1, the lipiodol+gelatin sponge, and the saline, before and after the interventional treatment, respectively.

The results show that, the liver tumors in each treatment group displayed a trend of growth, accompanied by central and peripheral irregular regional necrosis. Among them, tumor necrosis after treatment by embolization with the blood vessel embolic material of Example 1 and with the equal amount of lipiodol+gelatin sponge was more obvious, mostly manifested in flaky necrosis in the central region of the tumors. This indicates that the composition according to the present invention has a good embolization effect on liver tumors.

The invention claimed is:

1. A blood vessel embolic material comprising from 5 to 30 mg of poly(N-isopropylacrylamide-co-butyl methacrylate) crosslinked with N,N'-methylenebis(acrylamide), from 100 to 350 mg of an iodine-containing polyol in terms of iodine, and a dispersion medium;
   wherein the dispersion medium comprises from 0.1 to 30 mg of an electrolyte, and 0.1 to 10 mg of an iodine-free polyol;
   wherein all amounts are per mililiter of the blood vessel embolic material; and
   wherein the poly(N-isopropylacrylamide-co-butyl methacrylate) crosslinked with N,N'-methylenebis(acrylamide), is prepared by radical polymerization of a mixture comprising N-isopropylacrylamide, n-butyl methacrylate, and N,N'-methylenebis(acrylamide).

2. The blood vessel embolic material according to claim 1, wherein the electrolyte is at least one selected from the group consisting of sodium chloride, sodium hydroxide, calcium chloride, disodium hydrogen phosphate, sodium dihydrogen phosphate, and calcium disodium edetate.

3. The blood vessel embolic material according to claim 1, wherein the poly(N-isopropylacrylamide-co-butyl methacrylate) crosslinked with N,N'-methylenebis(acrylamide) has an intrinsic viscosity of 40 to 100 ml/g.

4. The blood vessel embolic material according to claim 1, wherein the dispersion medium further comprises a contrast agent, a pH regulator, and water.

5. The blood vessel embolic material according to claim 1, wherein the poly(N-isopropylacrylamide-co-butyl methacrylate) crosslinked with N,N'-methylenebis(acrylamide) is spherical.

6. The blood vessel embolic material according to claim 1, comprising:
   from 10 to 20 mg of the poly(N-isopropylacrylamide-co-butyl methacrylate) crosslinked with N,N'-methylenebis(acrylamide),
   from 0.1 to 30 mg of the electrolyte, and
   from 150 to 240 mg of the iodine-containing polyol in terms of iodine,
   per mililiter of the blood vessel embolic material.

7. The blood vessel embolic material according to claim 4, having a pH of 6.5 to 8.0.

8. The blood vessel embolic material according to claim 4, wherein the contrast agent includes an iodine-containing polyol, wherein the iodine-containing polyol is at least one of iohexol, ioversol, iopamidol, and iobitridol.

9. The blood vessel embolic material according to claim 4, wherein the pH regulator includes hydrochloric acid.

10. The blood vessel embolic material according to claim 5, wherein the iodine-free polyol includes at least one selected from the group consisting of tromethamine, mannitol, Tween-80, poly(ethylene glycol) 200, poly(ethylene glycol) 400, and poly(ethylene glycol) 600.

11. The blood vessel embolic material according to claim 1, further comprising a chemotherapeutic agent.

12. The blood vessel embolic material according to claim 4, wherein the chemotherapeutic agent is at least one selected from the group consisting of doxorubicin hydrochloride, epirubicin hydrochloride, mitomycin C and fluorouracil.

13. A method of treating a solid tumor in a patient in need thereof, comprising injecting a composition to an artery supplying the tumor, wherein the composition comprises the blood vessel embolic material according to claim 1.

* * * * *